US008557570B2

(12) United States Patent
Sahoo et al.

(10) Patent No.: US 8,557,570 B2
(45) Date of Patent: Oct. 15, 2013

(54) PUMPING AND FLOW CONTROL IN SYSTEMS INCLUDING MICROFLUIDIC SYSTEMS

(75) Inventors: Hemantkumar R. Sahoo, Houston, TX (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 745 days.

(21) Appl. No.: 12/312,348

(22) PCT Filed: Nov. 6, 2007

(86) PCT No.: PCT/US2007/023350
§ 371 (c)(1),
(2), (4) Date: Jan. 19, 2010

(87) PCT Pub. No.: WO2008/143638
PCT Pub. Date: Nov. 27, 2008

(65) Prior Publication Data
US 2010/0170572 A1 Jul. 8, 2010

Related U.S. Application Data

(60) Provisional application No. 60/857,468, filed on Nov. 6, 2006.

(51) Int. Cl.
*C12M 1/00* (2006.01)
*C12M 3/00* (2006.01)

(52) U.S. Cl.
USPC ........................... 435/289.1; 422/500; 137/14

(58) Field of Classification Search
USPC .................... 422/100, 113, 500; 137/14, 624; 435/289.1
See application file for complete search history.

(56) References Cited

U.S. PATENT DOCUMENTS

| | | | | |
|---|---|---|---|---|
| 2002/0153047 | A1 | 10/2002 | Parce et al. | |
| 2006/0002823 | A1* | 1/2006 | Feldstein | 422/100 |
| 2006/0275179 | A1* | 12/2006 | Viovy et al. | 422/100 |

FOREIGN PATENT DOCUMENTS

| | | |
|---|---|---|
| WO | WO 97/45644 | 12/1997 |
| WO | WO 2004/103566 A1 * | 12/2004 |
| WO | WO 2006/044571 | 4/2006 |
| WO | WO 2008/143638 | 11/2008 |

OTHER PUBLICATIONS

Atencia et al., "Steady flow generation in microcirculatory systems," *Lab on a Chip* 2006, vol. 6: 567-574.
Futterer et al., "Injection and flow control system for microchannels," *Lab Chip* 2004, vol. 4: 351-356.
Gunther et al., "Micromixing of Miscible Liquids in Segmented Gas-Liquid Flow," *Langmuir* 2005, vol. 21: 1547-1555.

(Continued)

*Primary Examiner* — Michael Hobbs
(74) *Attorney, Agent, or Firm* — Wolf, Greenfield & Sacks, P.C.

(57) ABSTRACT

The present invention generally relates to devices and methods for affecting the flow rate of fluid using pressure. The invention generally provides for controlled application of pressure to flowing fluids to control pressure and flow rates of those fluids, independent of location of the fluids relative to various devices. For example, in a series of devices, each connected to another via a conduit, pressure control units can be provided between devices to raise or lower pressure and/or flow rate of fluid flowing from one device to the next. In this way, a series of interconnected devices can be arranged such that inlet fluid pressure or flow rate of any individual device can be set independently of every other device.

19 Claims, 11 Drawing Sheets

(56) References Cited

OTHER PUBLICATIONS

Hessel et al. "Organic Synthesis with Microstructured Reactors," *Chem. Eng. Technol.* 2005, vol. 28(3): 267-284.

Jensen, "Microreaction engineering—is small better?" *Chemical Engineering Science* 2001, vol. 56: 293-303.

Kralj et al., "Integrated continuous microfluidic liquid-liquid extraction," *The Royal Society of Chemistry and Lab Chip* 2007, vol. 7: 256-263.

Rolland et al., "Solvent-Resistant Photocurable 'Liquid Teflon' for Microfluidic Device Fabrication," *J. Am. Chem. Soc.* 2004, vol. 126: 2322-2323.

Sahoo et al., "Multistep Continuous-Flow Microchemical Synthesis Involving Multiple Reactions and Separations," http://www3.interscience.wiley.com/journal/114281208/abstract?CRETRY=1&SRETRY=0, last accessed Jan. 11, 2010, 5 pgs.

Thayer, "Harnessing Microreactions" *Chemical & Engineering News* (May 30, 2005), vol. 83 (22): 43-52.

Unger et al., "Monolithic Microfabricated Valves and Pumps by Multilayer Soft Lithography," *Science* (Apr. 7, 2000), vol. 288: 113-116.

[No Author Listed], "Micropumps: Beating Heart of Microfluidics," Bartels Mikrotechnik, Aug. 31, 2006, available at http://web.archive.org/web/20060831231131/http://bartels-mikrotechnik.de/produkte/mikropumpe-lang-en.html/lang-en, last accessed Jan. 13, 2012, 2 pgs.

[No Author Listed], "Integrated Fluidic Circuits (IFCs) for the Life Sciences," Fluidigm® Corporation, Apr. 3, 2006, available at http://web.archive.org/web/20060403171516/http://fluidigm.com/index.html, last accessed Jan. 13, 2012, 1 pg.

International Search Report from PCT/US2007/023350, mailed Oct. 21, 2009.

International Preliminary Report on Patentability from PCT/US2007/023350, mailed Oct. 27, 2009.

Written Opinion from PCT/US2007/023350, mailed Oct. 27, 2009.

Sahoo, Hemantkumar, "Design and Operation of Microchemical Systems for Multistep Chemical Syntheses," Ph.D. Thesis, MIT, 2008.

* cited by examiner

PUMPING AND FLOW CONTROL IN SYSTEMS INCLUDING MICROFLUIDIC SYSTEMS

RELATED APPLICATIONS

This application is a national stage of International Patent Application No. PCT/US2007/023350, filed Nov. 6, 2007, which claims priority under 35 U.S.C. § 119(e) to U.S. Provisional Patent Application Ser. No. 60/857,468, filed Nov. 6, 2006, each of which is incorporated herein by reference in its entirety for all purposes.

FIELD OF THE INVENTION

The present invention generally relates to devices and methods for affecting flow rate of fluid using pressure.

BACKGROUND OF THE INVENTION

Microfluidic devices have potential applications in biotechnology, microchemical systems, fine chemicals industry, pharmaceuticals, fuel cells, microelectromechanical systems (MEMS), and the like. Recent research has focused on devices formed by the connection of a series of individual microfluidic systems to form an integrated or modular microchemical system, optionally with sensors and other means for online analysis, similar to a miniaturized chemical plant. For example, it would be advantageous to have the ability to perform a multi-step chemical synthesis using a series of microreactors and micro-phase-separators connected in series to form a chemical product. Systems such as these would reduce the time and cost of synthesizing various commercial products.

Insufficient attempts have been made to address the issues of connecting the individual devices in order to create a such "miniaturized chemical plants." This may be attributed to the lack of micro-versions of pumping devices used in conventional chemical industry. For example, current syringe pumps provide essentially the same fluid flow rate through all the connective devices, which often results in a pressure decay along the pressure profile the system. This limitation does not allow the connection of the series of devices, each having a different flow rate. Many current systems comprise a single pump attached at the beginning of a series of devices, such that the flow rate provided by the pump decays as it travels through each device. Additionally, the microfabricated valves and pumps produced using multilayered soft lithography often employ elastomers such as silicones that are not compatible with harsh chemicals. Moreover, these materials can only handle very small flow rates and volumes, and the flows often show fluctuations.

Accordingly, improved devices and methods are needed.

SUMMARY OF THE INVENTION

The present invention relates to fluid pressure regulators able to affect pressure of a chemically or biologically interacting fluid passing from a first chemical or biological processing device to a second chemical or biological processing device, comprising a pressure regulator inlet fluidly connected to the first chemical or biological processing device; a pressure regulator outlet fluidly connected to the second chemical or biological processing device; at least two enclosures, each enclosure constructed to contain the chemically or biologically interacting fluid, and each fluidly connected to both the pressure regulator inlet and the pressure regulator outlet; a source of a pressurizing fluid in communication with the at least two enclosures, whereby the pressurizing fluid applies pressure to the interacting fluid to urge movement of the interacting fluid relative to each respective enclosure through the outlet to the second processing device; and at least one one-way valve in a conduit between the pressure regulating inlet and the pressure regulating outlet, positioned to allow fluid flow preferentially in a direction from the inlet toward the outlet, wherein, in operation, the interacting fluid has a first pressure and/or flow rate in the pressure regulator inlet and a second pressure and/or flow rate in the pressure regulator outlet, wherein the second pressure and/or flow rate can be made by the device to be greater than the first pressure and/or flow rate.

The present invention also relates to fluid recirculation devices comprising a chemical or biological processing device comprising a processing inlet and a processing outlet, constructed and arranged to receive a chemically or biologically interacting fluid; a first enclosure fluidly connected to the processing inlet and a second enclosure fluidly connected to the processing outlet, each having a substantially constant set operating pressure range, wherein the operating pressure range of the first enclosure is, on average, greater than the pressure operating range of the second enclosure; and a regulating enclosure fluidly connected to the first enclosure and the second enclosure, wherein the regulating enclosure has an operating pressure range which spans the operating pressure ranges of the first enclosure and the second enclosure; and at least one source of a pressurizing fluid in communication with the regulating enclosure, and, optionally, at least one of the first enclosure and/or the second enclosure whereby the pressurizing fluid applies pressure to a chemically or biologically interacting fluid to urge movement of the interacting fluid relative to at least one respective enclosure, wherein, in operation, application of pressurizing fluid to the regulating enclosure over the regulating enclosure pressure range results in at least a first regulating enclosure pressure higher than the operating pressure ranges of the first and second enclosures and a second regulating enclosure pressure lower than the operating pressure ranges of the first and second enclosures, and the first and second enclosure operating pressure ranges are adjusted to maintain a first pressure and/or flow rate of the interacting fluid in the inlet of the processing device and a second pressure and/or flow rate in the outlet of the processing device within a range of difference which is less than the regulating enclosure pressure range.

The present invention also relates to fluid recirculation devices comprising a chemical or biological processing device comprising a processing inlet and a processing outlet, constructed and arranged to receive a chemically or biologically interacting fluid; a first enclosure fluidly connected to the processing inlet and a second enclosure fluidly connected to the processing outlet; and a regulating enclosure fluidly connected to the first enclosure and the second enclosure, wherein at least the regulating enclosure is connectable to a source of a pressurizing fluid, and each of the first, second, and regulating enclosures is connected to a pressure release valve to release pressurizing fluid.

Another aspect of the present invention provides methods for urging a chemically or biologically interacting fluid through a chemical or biological processing device with controlled flow rate and/or pressure differential across the device, comprising providing a chemical or biological processing device having an inlet and an outlet; providing a fluid pathway connecting the outlet of the device with the inlet of the device, wherein the fluid pathway comprises a first enclosure having an inlet, and an outlet fluidly connected to the inlet of the chemical or biological processing device, a second enclosure having an outlet, and an inlet fluidly connected to the outlet of chemical or biological processing device, and a regulating enclosure having an inlet fluidly connected to the outlet of the second enclosure and an outlet fluidly connected to the inlet of the first enclosure; regulating pressure of a pressurizing fluid in the regulating enclosure to provide a first pressure differential between all enclosures such that the regulating enclosure operates within a higher regulating pressure range, the first enclosure operates within a first pressure range lower than the higher regulating pressure range, and the second enclosure operates within a second pressure range lower than the first pressure range and, alternately, regulating pressure of a pressurizing fluid in the regulating enclosure to provide a second pressure differential between all enclosures such that the regulating enclosure operates within a lower regulating pressure range, the first enclosure operates within a first pressure range higher than the lower regulating pressure range, and the second enclosure operates within a second pressure range lower than the first pressure range, wherein a chemically or biologically interacting fluid can be urged by the device from the first enclosure, through a chemical or biological processing device, to the second enclosure.

The present invention also relates to systems comprising at least a first chemical or biological processing device and a second chemical or biological processing device, each including an inlet and an outlet, the inlet connectable to a source of a chemically or biologically interacting fluid; a conduit fluidly connecting the outlet of the first chemical or biological processing device to the inlet of the second chemical or biological processing device, wherein the conduit comprises an essentially rigid material; and a pressurizing fluctuation dampening device in association with the conduit, able to affect the pressure and/or flow rate of the interacting fluid at at least one point along the conduit between the outlet of the first processing device and the inlet of the second processing device, wherein the pressure fluctuation dampening device comprises at least one expandable volume fluidly connected to the conduit, the at least one expandable volume comprising a flexible material with a flexure resistance, such that, in operation, variations in pressure of interacting fluid passing through the conduit cause expansion and/or contraction of the expandable volume, thereby affecting the pressure and/or flow rate of the interacting fluid.

The present invention also provides fluid recirculation devices comprising a chemical or biological processing device comprising a processing inlet and a processing outlet, constructed and arranged to receive a chemically or biologically interacting fluid; a first enclosure and a second enclosure, each having a variable operating pressure range, wherein the operating pressure of the first enclosure can be set to be higher than that of the second enclosure so as to urge a chemically or biologically interacting fluid through the processing device; a first conduit fluidly connecting the first enclosure to the processing inlet and a second conduit fluidly connecting the second enclosure to the processing outlet, wherein the first conduit comprises an essentially rigid material; and a pressurizing fluctuation dampening device in association with either the first conduit, the second conduit, or both, able to affect the pressure and/or flow rate of the interacting fluid at at least one point along the conduit between the first enclosure and the processing inlet, wherein the pressure fluctuation dampening device comprises at least one expandable volume fluidly connected to the conduit, the at least one expandable volume comprising a flexible material with a flexure resistance, such that, in operation, variations in pressure of interacting fluid passing through the conduit cause expansion and/or contraction of the expandable volume, thereby affecting the pressure and/or flow rate of the interacting fluid.

The present invention also provides system comprising at least a first chemical or biological processing device, and a second chemical or biological processing device, each including an inlet and an outlet; a source of a chemically or biologically interacting fluid connected to the inlet of the first processing device; a conduit fluidly connecting the outlet of the first processing device to the inlet of the second processing device; and a pressurizing device in association with the conduit, able to increase the pressure and/or flow rate of fluid at at least one point between the outlet of the first processing device and the inlet of the second processing device, by application of a pressurizing fluid.

DETAILED DESCRIPTION

Figure 1A:
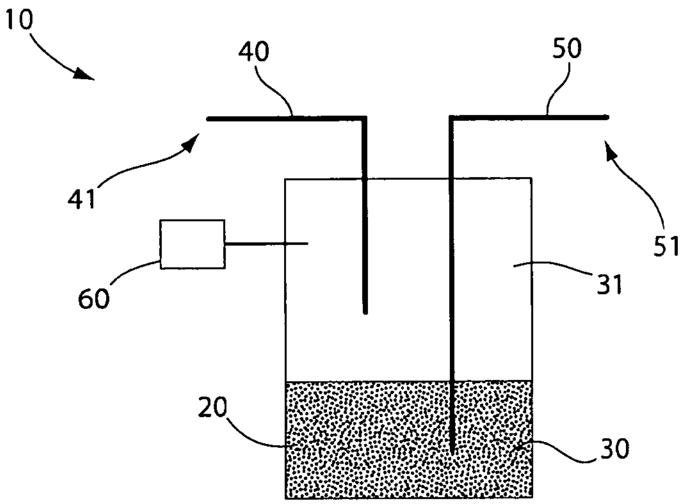
FIG. 1A shows a schematic representation of a pressure-driven flow system.

The present invention generally relates to devices and methods for affecting the flow rate of one or more fluids using pressure. The invention generally provides for controlled application of pressure to flowing fluids to control pressure and flow rates of those fluids, independent of location of the fluids relative to various devices. For example, in a series of devices, each connected to another via a conduit, pressure control units can be provided between devices to raise or lower pressure and/or flow rate of fluid flowing from one device to the next. In this way, a series of interconnected devices can be arranged such that inlet fluid pressure or flow rate of any individual device can be set independently of every other device.

Arrangements of the invention allow for control of fluctuation of pressure and/or flow rate in devices as well. For example, in some known pressure control devices, undesirable fluctuation in flow rate and/or pressure can exist. As will be seen from the invention as described below, these fluctuations can be lessened, or dampened, with the invention. Additionally, where fluctuations in pressure and/or flow rate are desired, or desirably increased, these can be effected by techniques and systems of the invention.

At many locations herein, "pressure and/or flow rate" of a fluid is discussed. As will be apparent from the description herein, techniques and systems of the invention allow for independent control of pressure, independent control of flow rate, or both. For example, in a series of interconnected devices, not only can fluid pressure at each inlet of each device be set independently of all others, but flow rate at the inlet of each device can be set independently of all others.

Another feature of the invention is the ability to establish recirculating chemical or biological reactive or interactive systems, in which fluid from the outlet of a device enters a pathway fluidly interconnected to the inlet of the same device. Fluid, upon exiting the outlet of the device, can be subjected to a variety of reaction conditions, or the like, with pressure and/or flow rate of the fluid established at any location between the outlet and the inlet independently of all other locations.

Note that, while microfluidic chemical or biological interactive systems are described herein in connection with many examples, in each instance where a microfluidic system is exemplified or described, a larger fluidic device can be used. Similarly, any of the devices in size larger than microfluidic devices are described, microfluidic devices can be used instead.

In some embodiments, the present invention provides devices and methods to facilitate constant fluid flow through a device, including constant recirculating fluid flow, as described more fully below. The present invention also provides devices and methods related to fluid pressure regulators which may increase the pressure and/or flow of a fluid in a device. One advantage of the invention may be the ability to connect a plurality of devices in a series, wherein the pressure and/or flow rate of each device may be controlled. That is, decay of the pressure and/or flow rate profile may be prevented. In some cases, the devices and methods described here may provide constant flow rate having substantially no fluctuation, or, fluctuation having a desired amplitude and frequency. The use of pressure to control fluid path may allow for greater flexibility in the design and construction of microfluidic devices.

The present invention may be advantageous in that the devices and methods described herein allow for control over the pressure and/or flow rate of a fluid at various locations in a multi-component reactor system. For example, a reactor system may comprise a series of processing devices, wherein a fluid sample or portion thereof may be processed (e.g., treated, reacted, separated, filtered, purified, etc.) at each processing device. Reactor systems such as these may be useful in, for example, continuous, multi-step chemical syntheses of organic compounds. Devices and method of the present invention may have the ability control the pressure and/or fluid at a particular processing device or between processing devices. In some cases, the reactor system may be maintained at a substantially constant flow rate, wherein the pressure profile of the system over the series of individual processing devices remains essentially constant. In some cases, the reactor system may employ controlled flow fluctuation at a particular processing device or between processing devices, wherein the flow fluctuation has a desired amplitude and frequency.

The present invention may also provide devices and method for the recirculation of fluids. For example, a device may comprise a processing device in association with a fluid recirculation device capable of maintaining an essentially constant pressure and/or flow rate through the processing device (or pressure and/or flow rate controlled in a different manner). This may be advantageous in systems where, for example, a time-delayed fluid flow may be required between two processing devices. In some cases, the fluid recirculation device may enhance the performance of the processing device. For example, the processing device may comprise a heterogeneous catalyst, wherein the yield of the chemical reaction catalyzed by the heterogeneous catalyst may be improved by the recirculation of the reactant fluid over the heterogeneous catalyst.

Another advantage of the present invention may be the ability to use a wide range of materials, including substantially rigid materials, for components of the devices (e.g., conduits, valves, enclosures, etc.). The use of pressure-driven flow in embodiments of the invention allow for the use of substantially rigid materials, such as steel, glass, and silicon nitride, for various components of the invention. In some embodiments, the use of rigid materials may be advantageous in that certain conditions, such as oxygen-free conditions, may be employed within various devices of the invention. Other systems which employ flexible and optionally elastomeric materials, such as PDMS, often exhibit high permeability to certain gases, such as oxygen, and other small molecules. In other embodiments, the use of pressure-driven flow may eliminate the need for external devices such as syringe pumps or HPLC pumps, which can simplify the overall system.

Generally, the present invention employs the use of pressure (specifically, control over a pressure differential between different points in a system, or multiple such differentials) to urge the movement of fluid through various components of the device. For example, some embodiments of the invention may establish a particular pressure differential between two enclosures, wherein the enclosures are fluidly connected by a conduit. The pressure differential may be selected to urge movement of a fluid contained within one of the enclosures, from one enclosure to the other enclosure. Movement of a fluid may be further controlled via the placement of one-way valves at a point between enclosures, wherein the one-way valves are fluidly connected to the conduit. For example, an enclosure may comprise an inlet, an outlet, and a fluid contained within the enclosure, wherein the pressure of the enclosure may be increased, i.e., via introduction of a pressurizing fluid to the enclosure, to urge or force the fluid to be moved through the outlet. FIG. 1A shows an illustrative embodiment of a pressure-driven flow system useful in the invention. System 10 is, in isolation, known in the art, but its use in combination with other aspects described herein is inventive. System 10 comprises an enclosure 20, inlet 41, and an outlet 51. The enclosure contains an interior space 30 which can contain an interacting fluid (also referred to as an interacting fluid 30), and a different interior space 31, shown in FIG. 1A to be above space 30, generally filled with a second fluid which can be a pressurizing fluid (used to apply pressure to an interacting fluid in space 30 to effect flow). Hereinafter, "interacting fluid" may be used interchangeably with space 30, and "pressurizing fluid" may be used interchangeably with space 31, because in most embodiments these fluids fill these spaces, respectively (although this is not necessary, and the invention can be used differently). In most embodiments described herein, the interacting fluid is a liquid and the second fluid, or pressurizing fluid, is a gas (such as air, nitrogen, argon, carbon dioxide, or the like), although those of ordinary skill in the art will recognize that any of a variety of different fluids can be used in association with the invention so long as they are sufficiently immiscible with each other. Where the fluids have densities which would cause them to be inverted with respect to each other with reference to FIG. 1A (e.g., where pressurizing fluid would settle into space 30, and interacting fluid would reside in some or all of space 31), then the entire device of FIG. 1A itself can be inverted for proper operation.

System 10 includes a conduit 40 connecting inlet 41 with space 31, and a conduit 50 connecting space 30 with outlet 51. Enclosure 20 may be fluidly connected to a source 60 of a pressurizing fluid. In operation, interacting fluid may be introduced into enclosure 20 via inlet 41 at a first pressure and/or flow rate, and may reside in some or all of space 30 (or a larger space). Introduction of a pressurizing fluid to enclosure 20 via source 60 may increase the pressure of enclosure 20, whereby a pressurizing fluid applies pressure to fluid 30 contained within enclosure 20 to urge movement of fluid 30 through conduit 50 toward outlet 51. The use of systems such as system 10, in the context of, for example, microfluidic devices, optionally in combination with other features described herein, may allow a device to maintain a constant flow rate and/or other desired flow rate.

Note that in various embodiments, for simplicity, inlet 41 and outlet 51 may be used interchangeably with conduit 40 and conduit 50, respectively, and their analogous components in other arrangements described in other figures.

Figure 1B:
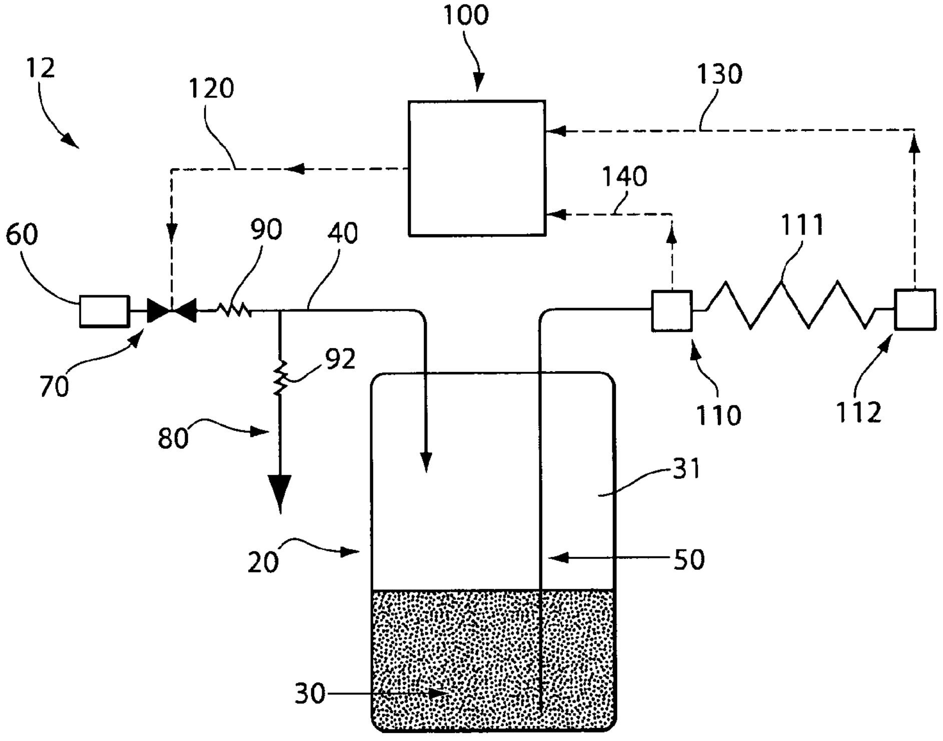
FIG. 1B shows a schematic representation of a pressure-driven flow system.

The pressure-driven flow system may further comprise other components useful in modulating the pressure and/or flow rate of the system. As shown in FIG. 1B, a valve 70 may be positioned between source 60 and conduit 40 to adjust pressure of the pressurizing fluid from source 60. A pressure release pathway 80 may be fluidly connected to conduit 40, such that pressurizing fluid may be released via pressure release pathway 80 to modulate the pressure of the pressurizing fluid from source 60 prior to introduction into enclosure 20. Pressure resistance controls 90 and 92, in conduits 40 and 80, respectively, may serve to modulate the pressure of the pressurizing fluid within enclosure 20 as supplied by source 60. For example, where valve 70 is a simple on/off valve (valve 70 can also be a variable flow or variable pressure valve), resistor 90 can modulate the "on" valve position to lessen the pressure applied to enclosure 20. Additionally, resistor 92 can act to maintain sufficient pressure in conduct 40, but to bleed off pressurizing fluid through pressure release pathway 80 at or above a threshold pressure. System 12 may further comprise one or more pressure sensors downstream of outlet 50, and a control system in which a signal from a monitor(s) is relayed to an actuator to control inlet pressure via inlet 40. As illustrated, pressure sensors 110 and 112 are provided, respectively, upstream and downstream of a chemical or biological interacting device 111, which itself is downstream of outlet 50 of the enclosure. These sensors can determine at least one of pressure and/or flow rate of interacting fluid 30 at their respective locations, and can determine pressure drop between them, i.e., pressure drop across device 111. A controller processor 100, which can be of conventional electronics and/or computer control, may be arranged to be responsive to a signal from, for example, valve 70 and/or pressure sensors 110 and 112, such that the pressure and/or flow rate of the pressurizing fluid introduced into chamber 20 may be adjusted. As illustrated, sensors 110 and 112 provide signals 140 and 130, respectively, to processor 100, which controls valve 70 via signal/actuation 120.

In some cases, the present invention provides systems comprising at least a first chemical or biological processing device and a second chemical or biological processing device. Each processing device may include an inlet and an outlet. A conduit which fluidly connects the outlet of the first processing device to the inlet of the second processing device may also be included. The system can further comprise a source of a chemically or biologically interacting fluid connected to the inlet of the first processing device, and a pressurizing device in association with the conduit. The pressurizing device may be able to increase the pressure and/or flow rate of fluid at at least one point between the outlet of the first processing device and the inlet of the second processing device, by application of a pressurizing fluid. In some cases, the pressure and/or flow rate of fluid, such as interacting fluid, can be adjusted at a point between the first and second chemical or biological processing devices, or at a point within a single chemical biological processing device. The pressure and/or flow rate of fluid in the system may undergo less fluctuation than in any essentially identical system lacking the pressurizing device, under essentially identical conditions. In some cases, application of the pressurizing fluid may effect the flow rate of the interacting fluid. In some cases, application of the pressurizing fluid may effect the rate of pressure change of the interacting fluid. The pressurizing device may be a fluid regulator device and/or a fluid recirculation device, as described herein. In some cases, the system may be a microfluidic system.

Figure 2A:
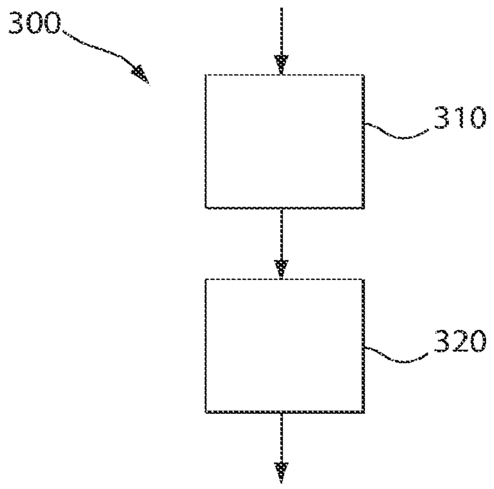
Fig. 2A PRIOR ART
FIG. 2A shows a schematic representation of a series of reactors.
Figure 2B:
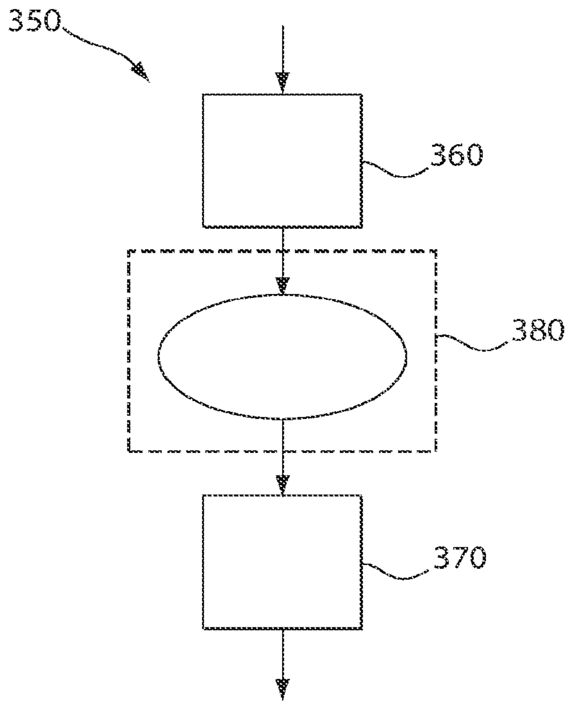
FIG. 2B shows a schematic representation of a pressure-driven flow system comprising a series of reactors and an intermediary pumping device.

Some embodiments of the present invention provide devices useful as pumping devices in a system including more than one chemical or biological interacting system. In some cases, the device may be used as an intermediate pumping device between a first processing device and a second processing device to maintain a particular pressure and/or flow to the second processing device. In some cases, the pressure and/or flow to the second processing device may be greater than the pressure and/or flow to the first processing device. In some cases, the pressure and/or flow to the second processing device may be lower than the pressure and/or flow to the first processing device. Devices such as this may be useful for maintaining a desired pressure and/or flow rate at various points in a system, such as a multi-component system comprising multiple processing devices. For example, in a typical prior art system including multiple devices arranged in fluidic series, as shown in FIG. 2A, system 300 comprises a device 310 fluidly connected to a device 320. An interacting fluid may be introduced to device 310 at a first pressure and/or flow rate, and, upon transfer of the interacting fluid from device 310 to device 320, the pressure and/or flow rate of the interacting fluid may decay. That is, the pressure profile of device 300 may decay along various devices of system 300 according to inherent fluid dynamic properties of the device. In contrast, system 350 of the present invention, as shown in FIG. 2B, comprises an intermediate pumping device 380 positioned in between and fluidly connected to device 360 and device 370. The presence of pumping device 380 allows for the control of the pressure and/or flow rate of interacting fluid that is introduced to device 370. For example, interacting fluid may be introduced to device 360 at a particular pressure and/or flow rate, wherein the interacting fluid is transferred from device 360, via an outlet, at a reduced pressure and/or flow rate. Pumping device 380 may adjust the pressure and/or flow rate of the interacting fluid such that the interacting fluid is transferred to device 370 at a desired pressure and/or flow rate. As described herein, the pressure and/or flow rate of interacting fluid that is introduced to device 370 may have a pressure and/or flow rate which is greater, lower, or the same as the pressure and/or flow rate of interacting fluid being introduced to device 360. Pumping device 380 can be any of a variety of devices, for example, a device as described above in connection with FIG. 1A, or as described below in connection with FIG. 3, or the like.

In some embodiments, the present invention provides systems comprising at least a first chemical or biological processing device and a second chemical or biological processing device, each including an inlet and an outlet, and a source of a chemically or biologically interacting fluid connected to the inlet of the first processing device. The system may further comprise a conduit fluidly connecting the outlet of the first device to the inlet of the second processing device, and a pressurizing device in association with the conduit. The pressurizing device may be capable of increasing the pressure and/or flow rate of fluid at at least one point between the outlet of the first processing device and the inlet of the second processing device, by application of a pressurizing fluid.

In some cases, the pressurizing device may be a fluid pressure regulator capable of affecting pressure of a chemically or biologically interacting fluid passing from a first chemical or biological processing device to a second chemical or biological processing device. The fluid pressure regulator may comprise a pressure regulator inlet fluidly connected to the first chemical or biological processing device, a pressure regulator outlet fluidly connected to the second chemical or biological processing device, and at least two enclosures. The enclosures may be constructed to contain the chemically or biologically interacting fluid and may be fluidly connected to both the pressure regulator inlet and the pressure regulator outlet. The enclosures may be arranged to receive the chemically or biologically interacting fluid from the first chemical or biological processing device.

The fluid pressure regulator may further comprise a source of a pressurizing fluid (e.g., gas) in communication with the at least two enclosures, whereby the pressurizing fluid applies pressure to the interacting fluid to urge movement of the interacting fluid relative to each respective enclosure through the outlet to the second processing device. For example, in operation, the interacting fluid may have a first pressure and/or flow rate in the pressure regulator inlet and a second pressure and/or flow rate in the pressure regulator outlet, wherein the second pressure and/or flow rate can be made by the device to be greater than the first pressure and/or flow rate. This pressure differential may facilitate movement of the interacting fluid from the enclosure to the second chemical or biological processing device.

In some cases, an enclosure may further comprise a pressure release valve, and/or other pressure resistance controls, for modulating the pressure within the enclosure. In some embodiments, the enclosure may be useful as a gas-liquid separator. For example, an interacting fluid comprising a gas may be introduced into the enclosure, wherein the gas may be separated from the interacting fluid via the pressure release valve. In illustrative embodiments, the first chemical or biological processing device may interact with the interacting fluid to produce a chemical product and a undesired, gaseous side product, such as nitrogen, for example. Removal of the side product may be required to purify the interacting fluid before transfer to the second chemical or biological processing device. Upon introduction of the interacting fluid comprising the gaseous side product into an enclosure of fluid pressure regulator, the side product may be removed via the pressure release valve, such that the purified interacting fluid may then be transferred to the second chemical or biological processing device.

Figure 3A:
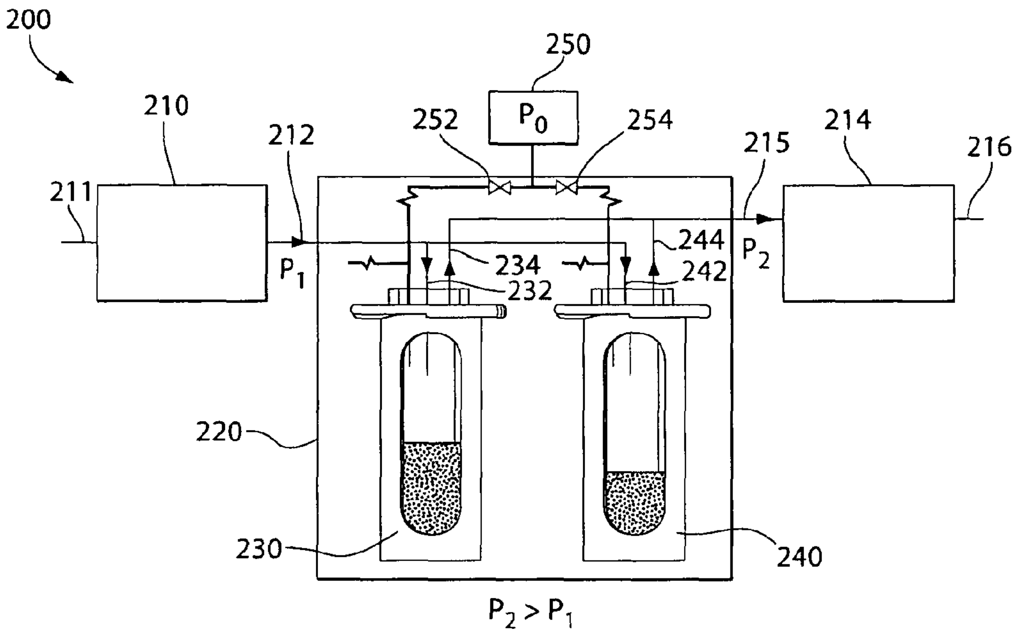
FIG. 3A shows a schematic representation of a pressure-driven flow system comprising a series of reactors and an intermediary pumping device to provide constant flow rate between devices, according to one embodiment of the invention.

One intermediate pumping device of the invention is illustrated in FIG. 3A. In this illustrative embodiment, system 200 comprises a device 210 and a device 214 fluidly connected to one another via intermediate pumping device, or pressure regulator 220. Device 210 comprises inlet 211 and outlet 212, and device 214 comprises inlet 215 and outlet 216, wherein outlet 212 is fluidly connected to inlet 215 via pressure regulator 220. The pressure regulator comprises an enclosure 230 and an enclosure 240, each of which is fluidly connected to inlet 212 and outlet 215. Enclosure 230 comprises an inlet 232, which is fluidly connected to outlet 212 such that interacting fluid is transferred from device 210 via outlet 212 to enclosure 230, via inlet 232. Enclosure 230 comprises outlet 234, which is fluidly connected to inlet 215, whereby interacting fluid can be moved from enclosure 230 via outlet 234 to device 214 via inlet 215. Enclosure 240 comprises an inlet 242, which is fluidly connected to outlet 212 such that interacting fluid can be transferred from device 210 via outlet 212 to enclosure 240, via inlet 242. Enclosure 240 comprises outlet 244, which is fluidly connected to inlet 215, whereby interacting fluid can be moved from enclosure 240 via outlet 244 to device 214 via inlet 215.

System 200 further comprises a source of pressurizing fluid 250 in communication with both enclosure 230 and enclosure 240. Source 250 may be constructed and arranged such that the flow of pressurizing fluid to enclosure 230 and/or enclosure 240 may be modulated via on/off valves, pressure release conduits, pressure resistance controls, and the like. For example, system 200 may comprise valves 252 and 254 positioned at a point between enclosures 230 and 240, respectively, and source 250. In operation, assuming enclosure 240 is in a relatively high pressure state and interacting fluid is being driven from enclosure 240 into device 214, when valve 252 is positioned to allow pressurizing fluid to flow from source 250 to enclosure 230, thereby increasing the pressure of enclosure 230, valve 254 is positioned such that substantially no pressurizing fluid flows from source 250 to enclosure 240. In this arrangement, enclosure 230 may be receiving interacting fluid from device 210 as it is receiving pressurizing fluid from source 250 (e.g., may become pressurized), while enclosure 240, at relatively higher pressure (from a previous pressurizing step) transfers interacting fluid to device 214. Once enclosure 230 is pressurized, e.g. to an extent greater than enclosure 240, valve 254 may be positioned to allow pressurizing fluid to flow from source 250 to enclosure 240, thereby increasing the pressure of enclosure 240, with valve 252 positioned such that substantially no pressurizing fluid flows from source 250 to enclosure 230. During this portion of the cycle of the device, enclosure 240 may receive interacting fluid from device 210 and/or may receive pressurizing fluid from source 250 (e.g., may become pressurized), while enclosure 230 transfers interacting fluid to device 214. At least one one-way fluid valve exists in the system and, as illustrated, one-way fluid valves exist, at least, in each conduit delivering fluid from device 210 into each of enclosures 230 and 240, and in each conduit delivering fluid from each of enclosures 230 and 240 to device 214. Note also, in the embodiment illustrated in FIG. 3, the presence of a pressurizing fluid release conduit and accompanying resistance unit connected to each conduit which connects pressurizing fluid source 350 with each enclosure, i.e., each enclosure can be pressurized by a conduit system as illustrated in FIG. 1B, relating the enclosure to a pressure source. These systems find analogous arrangements elsewhere in the figures.

Device 200 can be controlled, in terms of flow of pressurizing fluid into either or both of enclosures 230 and 240, and additional enclosures, if desired, pressure upstream of device 210, and/or pressure downstream of device 214 (each controlled, for example, by any type of intermediate pump or pressure control device), to control flow of fluid from device 210 into either enclosure, and from either enclosure into device 214. In one arrangement, pressure is applied by a simple switch valve from source 210 alternately into enclosures 230 and 240. At or above a threshold level of pressure in either enclosure, interacting fluid is driven from that enclosure into device 214, and, at or below a threshold level of pressure in either enclosure, interacting fluid is driven from device 210 into that enclosure. Thus, interacting fluid may flow from device 210, via the pressure regulator 220, to device 214 within an operating flow rate range with reduced or minimal fluctuation in pressure and/or flow rate, and since absolute pressure in each enclosure can be controlled, the process can proceed independent of pressure upstream of device 210 or downstream of device 214.

In some cases, the operating flow rate of device 200, or other devices or systems of the invention, may be a substantially constant flow rate. That is, interacting fluid may be introduced to device 210 via inlet 211 at a particular pressure and/or flow rate, wherein, in the absence of a pressure regulating device, the pressure of the interacting fluid may drop or decay upon exiting the device 210. Thus, in the absence of a pressure regulator, the interacting fluid may be transferred to device 214 via inlet 215 at a significantly reduced pressure. However, in the presence of pressure regulator 220, interacting fluid may be transferred from device 210 to device 214 wherein the inlet pressure of both inlets 211 and 215 may remain substantially constant.

Figure 3B:
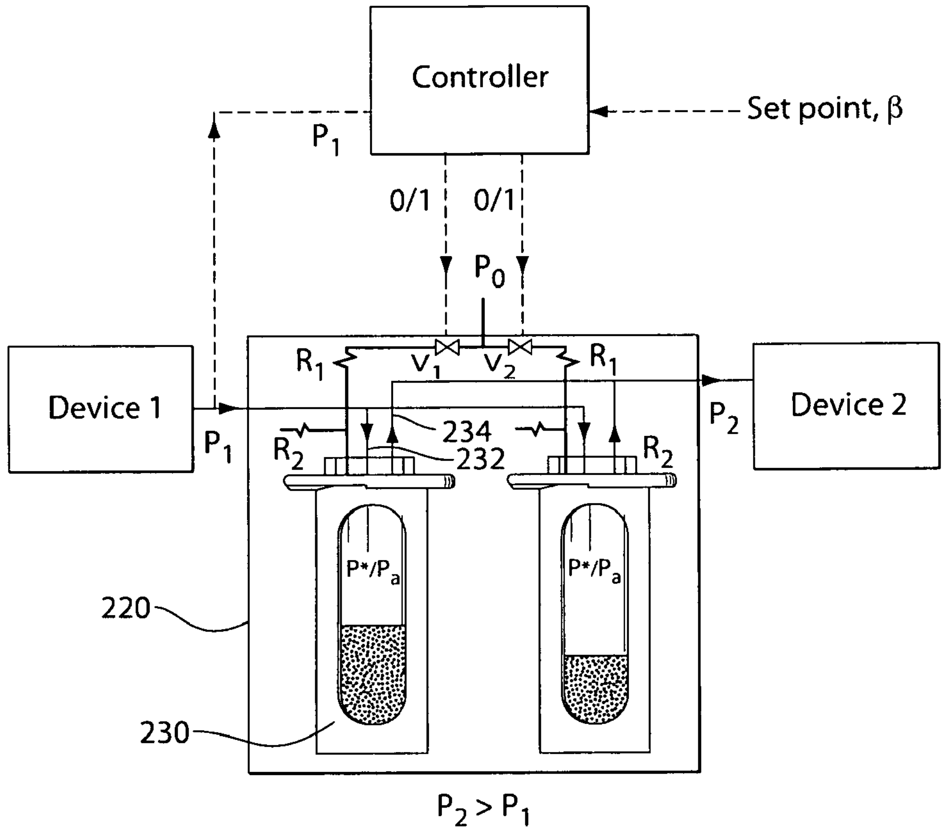
FIG. 3B shows a schematic representation of a pressure-driven flow system comprising a controller unit for regulating one or more valves of the system, according to one embodiment of the invention.

FIG. 3B shows a schematic representation of a pressure-driven flow system comprising a controller processor for regulating one or more valves of the system, according to one embodiment of the invention. The controller processor may be arranged to be responsive to a signal from, for example, valve 252, valve 254, outlet 212, such that the pressure and/or flow rate of the pressurizing fluid introduced into enclosures 230 and 240 may be adjusted.

In some embodiments, the present invention comprises systems comprising at least a first chemical or biological processing device and a second chemical or biological processing device, as described herein, and a conduit fluidly connecting the outlet of the first chemical or biological processing device to the inlet of the second chemical or biological processing devices, wherein the conduit comprises an essentially rigid material. The system may further comprise a pressurizing fluctuation dampening device in association with the conduit, wherein the pressurizing fluctuation dampening device is able to effect the pressure and/or flow rate of the interacting fluid at at least one point along the conduit between the outlet of the first processing device and the inlet of the second processing device. The pressure of fluctuation dampening device may comprise at least one expandable volume fluidly connected to the conduit. The at least one expandable volume may comprise a flexible material with a flexure resistance such that, in operation, variations in pressure of interacting fluid passing through the conduit cause expansion and/or contraction of the expandable volume, thereby effecting the pressure and/or flow rate of the interacting fluid.

In some cases, the system further comprises at least one one-way valve in the conduit positioned at a point between the first and second chemical or biological processing device, wherein the valve is positioned to allow fluid flow preferentially in a direction from the first chemical or biological processing device towards the second chemical or biological processing device. In some embodiments, the pressure of the fluctuation dampening devices comprises a plurality of expandable volumes fluidly connected to the conduit and/ optionally at least one one-way valve positioned at a point between a first expandable volume and a second expandable volume adjacent to the first expandable volume. The valve may be a continuous valve or a non-continuous valve.

In some cases, the present invention provides fluid recirculation devices comprising a chemical or biological processing device comprising a processing inlet and a processing outlet, when the processing device may be constructed and arranged to receive a chemically or biologically interacting fluid. A fluid recirculation device may comprise a first enclosure fluidly connected to the processing inlet and a second enclosure fluidly connected to the processing outlet wherein each enclosure has a substantially constant set operating pressure range. In some cases, the operating pressure range of the first enclosure may be, on average, greater than the pressure operating range of the second enclosure. This may allow transfer of an interacting fluid from the first enclosure through the processing device, and to the second enclosure. The fluid recirculation device may further comprise a regulating enclosure fluidly connected to the first enclosure and the second enclosure, wherein the regulating enclosure has an operating pressure range which spans the operating pressure ranges of the first enclosure on the second enclosure. The fluid recirculation device further comprises at least one source of a pressurizing fluid in communication with the regulating enclosure and, optionally, at least one of the first enclosure and/or second enclosure whereby the pressurizing fluid applies pressure to a chemically or biologically interacting fluid to urge movement of the interacting fluid relative to at least one respective enclosure.

For example, in operation, application of pressurizing fluid to the regulating enclosure over the regulating enclosure pressure range results in at least a first regulating enclosure pressure higher than the operating pressure ranges of the first and second enclosures and, alternately, a second regulating enclosure pressure lower than the operating pressure ranges of the first and second enclosures. The first and second enclosure operating pressure ranges may be adjusted to maintain a first pressure and/or flow rate of the interacting fluid in the inlet of the processing device, and a second pressure and/or flow rate in the outlet of the processing device within a range of difference which is less than the regulating enclosure pressure range. In some cases, in operation, the first, second, and regulating enclosures may be maintained each within their respective pressure ranges to cause the pressurizing fluid to urge the interacting fluid from the first enclosure, through the chemical or biological processing device, and to the second enclosure. In some cases, the pressurizing fluid urges the interacting fluid from the regulating enclosure to the first enclosure, and from the first enclosure through the chemical or biological processing device and to the second enclosure. In some cases, the pressurizing fluid urges the interacting fluid from the regulating enclosure to the first enclosure, and from the first enclosure through the chemical or biological processing device and to the second enclosure, and from the second enclosure to the regulating enclosure.

At least one one-way valve may be placed at any point within the fluid recirculation device to facilitate fluid flow in a preferential direction. For example, the fluid recirculation device may comprise at least one one-way valve in a conduit between (e.g., fluidly connecting) the regulating enclosure and the first enclosure, wherein the valve is positioned to allow fluid flow preferentially in a direction from the regulating enclosure toward the first enclosure. At least one one-way valve may also be placed in a conduit between the first enclosure and the processing inlet, wherein the valve is positioned to allow fluid flow preferentially in a direction from the first enclosure toward the processing inlet. In some cases, at least one one-way valve may also be placed in a conduit between the second enclosure and the processing outlet, positioned to allow fluid flow preferentially in a direction from the processing outlet toward the second enclosure. In some cases, at least one one-way valve may be placed in a conduit between the second enclosure and the regulating enclosure positioned to allow fluid flow preferentially in the direction from the second enclosure toward the regulating enclosure. The valve may be a continuous or a noncontinuous valve.

Figure 4:
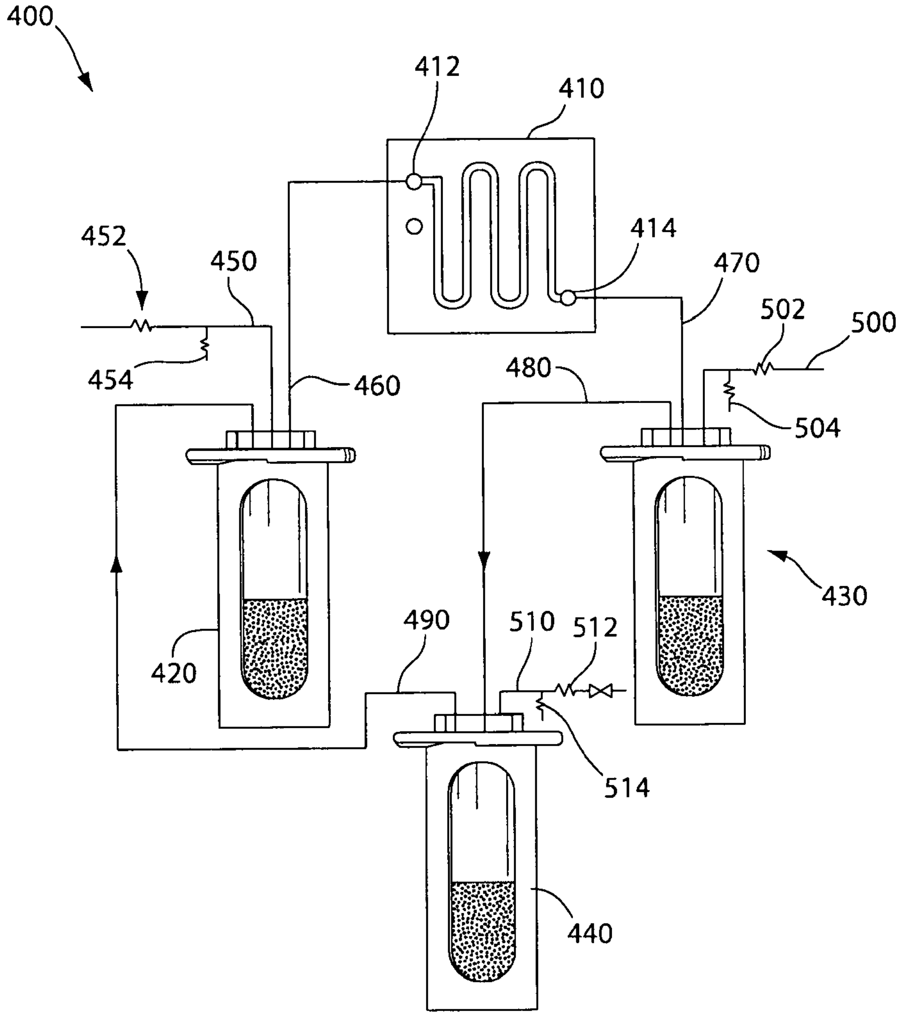
FIG. 4 shows a schematic representation of a pressure-driven flow system for the recirculation of fluid, according to one embodiment of the invention.

FIG. 4 shows a recirculation device according to one embodiment of the invention. Recirculation device 400 comprises a processing device 410 having a processing inlet 412 and a processing outlet 414. Processing inlet 412 may be fluidly connected to an enclosure 420, and processing outlet 414 may be fluidly connected to an enclosure 430. Enclosure 420 and enclosure 430 may be fluidly connected via a regulating enclosure 440. In operation, regulating enclosure 440 may contain a fluid to be transferred to processing device 410. A pressurizing fluid may be introduced via inlet 510 to regulating enclosure 440, to increase the pressure of regulating enclosure 440 within an operating pressure range. The operating pressure range may be optionally modulated via pressure regulator 512 and/or pressure release valve 454. Once pressurized, enclosure 440 may then transfer fluid via conduit 490 to enclosure 420. In order for this transfer of fluid to occur, enclosure 440 may be pressurized to have an operating pressure range greater than the operating pressure range of enclosure 420.

The first, second, and regulating enclosures may be maintained, each within the respective pressure ranges, to cause transfer of interacting fluid from enclosure 440 to enclosure 420, via conduit 490, from enclosure 420 through processing device 410 to enclosure 430, and from enclosure 430 to enclosure 440 via conduit 480, all with desired pressure drop across device 410. In order for transfer of fluid to occur from enclosure 430 to enclosure 440, enclosure 440 may have an operating pressure range lower than the operating pressure range of enclosure 430. Thus, enclosure 440 may be switchable between a high operating pressure range, such that fluid may be transferred from enclosure 440 to enclosure 420, and a low operating pressure range, such that fluid may be transferred from enclosure 430 to enclosure 440. The first, second, and regulating enclosures may be maintained such that pressure and/or fluid flow of interacting fluid passing through processing device 410 may remain essentially constant, or the pressure drop across device 410 can fluctuate in a controlled manner. Notably, the pressure and/or flow rate at the inlet of the processing device and the pressure and/or flow rate at the outlet of the processing device may be maintained within a range of difference which is less than the overall operating pressure range of enclosure 440. As noted elsewhere, one or more of enclosures 420, 430, and/or 440 may be reactive (e.g., may be a chemical or biological processing device) or may otherwise affect interacting fluid passed therethrough.

Figure 5:
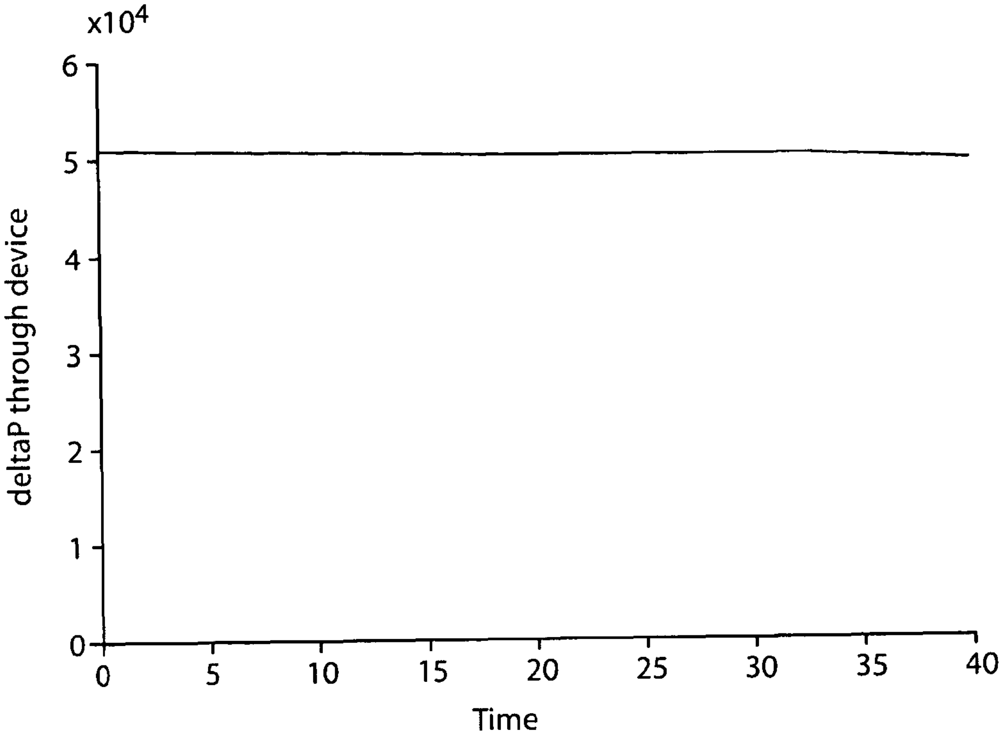
FIG. 5 shows the flow rate of a pressure-driven flow system for the recirculation of fluid, as a function of time.

FIG. 5 shows the ideal flow rate of a pressure-driven flow system for the recirculation of fluid as described herein in FIG. 4, as a function of time, wherein the pressure and/or flow rate of the processing device remains essentially unchanged via careful control of pressures within the various enclosures of FIG. 4, including when switching the regulating enclosure from high to low pressure ranges.

Recirculation device 400 may further comprise various pressure release valves and/or resistors to modulate the pressure of pressurizing fluid applied to various components of the device 400. For example, enclosure 420 may be fluidly connected to a pressure release valve 454 and a resistor 452, able to modulate the pressure applied to enclosure 420, as described herein. Similarly, enclosure 430 may comprise pressure release valve 504 and resistor 502, and enclosure 440 may comprise pressure release valve 514 and resistor 512.

In some cases, a fluid recirculation device may comprise one or more pressure fluctuation dampening devices, each comprising a plurality of expandable volumes, as described herein. In one embodiment, interacting fluid may be introduced to the conduit with a first pressure and/or flow rate and may interact with a first expandable volume to alter (e.g., reduce, or otherwise modulate) the first pressure and/or flow rate to produce a second pressure and/or flow rate. The interacting fluid may then interact with a second expandable volume at the second pressure and/or flow rate, wherein the second expandable volume is located at a point downstream from the first expandable volume. The various expandable volumes may serve to modulate (e.g., reduce, dampen) fluctuation in the pressure and/or flow rate of the interacting fluid such that the interacting fluid may be introduced to the processing device, via the processing inlet, at a selected pressure and/or flow rate.

In some cases, the system further comprises at least one one-way valve positioned at a point between the first chemical or biological processing device and the second chemical or biological processing device, wherein the valve is positioned to allow fluid flow preferentially in a direction from the first chemical or biological processing device toward the second chemical or biological processing device. For example, the one one-way valve may be positioned at a point between a first expandable volume and a second expandable volume adjacent to the first expandable volume.

Figure 6:
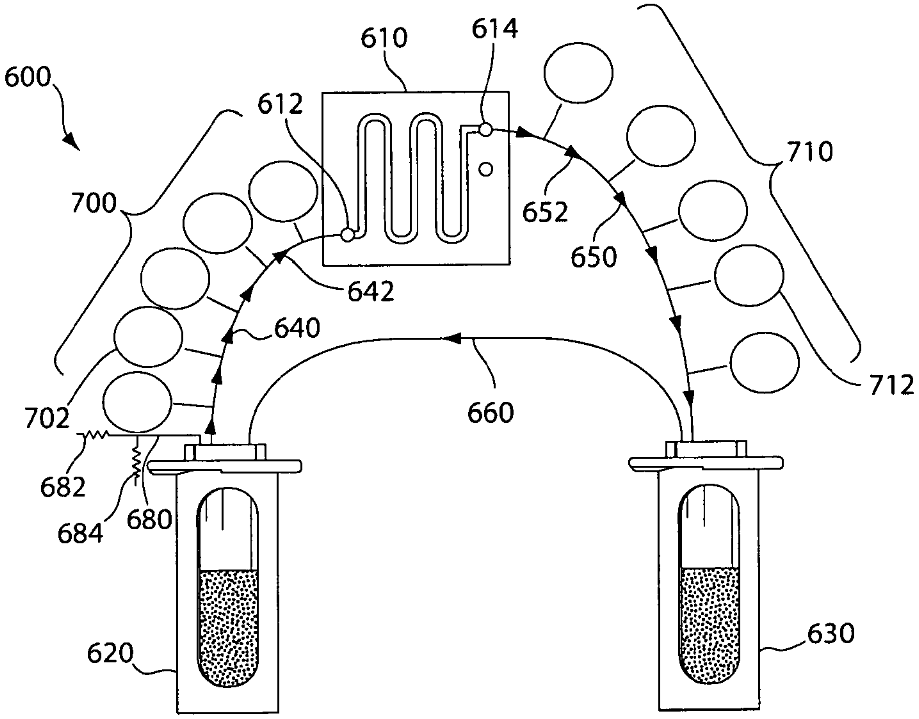
FIG. 6 a schematic representation of a pressure-driven flow system having variable volume units, according to one embodiment of the invention.

As shown by the illustrative embodiment in FIG. 6, device 600 comprises a processing device 610 comprising a processing inlet 612 and a processing outlet 614. Processing device 610 may be constructed and arranged to receive a chemically or biologically interacting fluid. Device 600 further comprises enclosure 620 and enclosure 630, each having a variable pressure range, wherein the operating pressure of the first enclosure may be set to be higher than that of second enclosure, so as to urge a chemically or biologically interacting fluid through the processing device. Enclosure 620 may be fluidly connected to the processing inlet 612 via a conduit 640, wherein conduit 640 may comprise an essentially rigid material. Processing outlet 614 may be fluidly connected to enclosure 630 via conduit 650, wherein conduit 650 may comprise an essentially rigid material. Enclosures 620 and enclosure 630 may be fluidly connected via conduit 660, which may also comprise an essentially rigid material. Device 600 may further comprise a source of a pressurizing fluid in association with at least one enclosure, and may further comprise various pressure release valves and/or resistors to modulate the pressure applied to the enclosure. For example, enclosure 620 may be fluidly connected to a source of a pressurizing fluidly connected to a source of a pressurizing fluid via conduit 680, and may comprise pressure release valve 684 and resistor 682.

Figure 7:
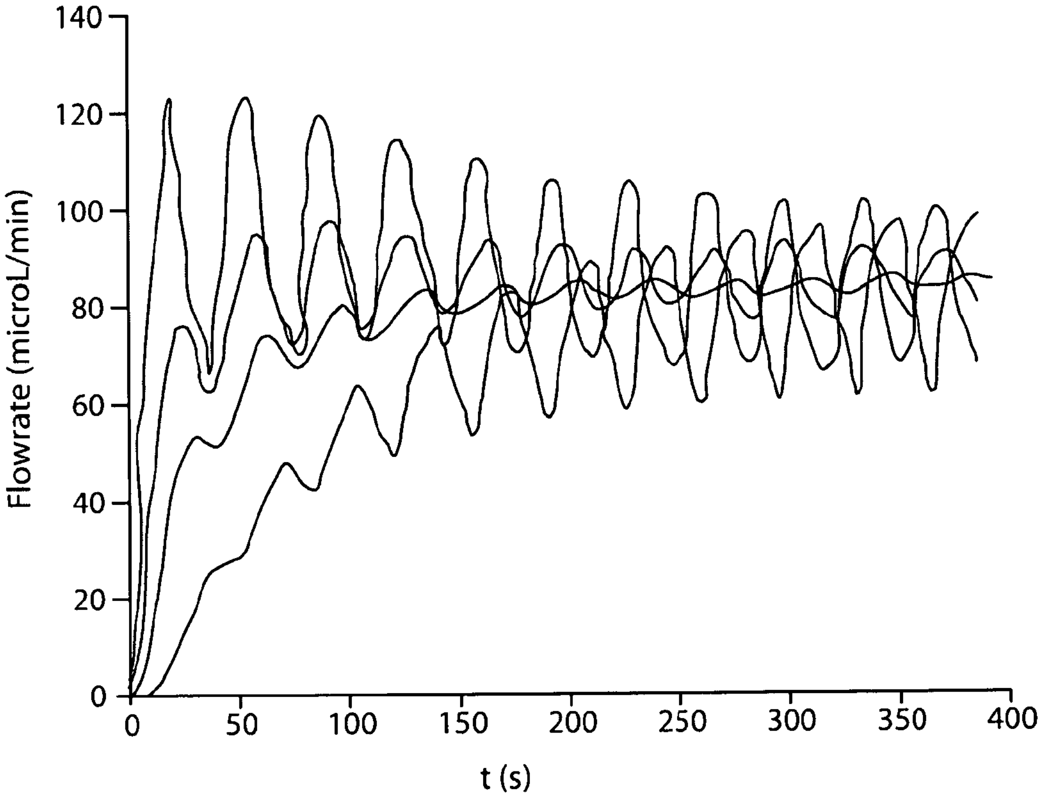
FIG. 7 shows the flow rate of a pressure-driven flow system having variable volume units, as a function of time.

Device 600 may further comprise a pressurizing fluctuation dampening device in association with either conduit 640, conduit 650, or both, such that the pressurizing or fluctuation dampening device may be able to effect the pressure and/or flow rate of the interacting fluid at at least one point along the conduit. For example, conduit 640 may further comprise a plurality 700 of expandable volumes fluidly connected to conduit 640. Conduit 650 may comprise a plurality 710 of expandable volumes fluidly connected to conduit 650. One or more one-way valves may be positioned along the conduit, such as valve 642 and valve 652, wherein the valve may be positioned between two adjacent expandable volumes. In operation, a pressurizing fluid may be applied to enclosure 620 to urge movement of interacting fluid from enclosure 620 to processing inlet 612 via conduit 640. Interacting fluid may pass through conduit 640 and may cause expansion and/or contraction of the expandable volumes, such that fluctuations in the pressure and/or flow rate of the interacting fluid may be reduced prior to introduction of the interacting fluid to processing inlet 612. That is, the plurality 700 of expandable volumes may provide a time-delayed flow of interacting fluid such that the pressure and/or flow rate of interacting fluid through processing device 610 may be modulated. Similarly, the plurality 710 of expandable volumes may be used to modulate the pressure and/or flow rate of interacting fluid flowing through conduit 650. FIG. 7 shows the flow rate of a fluid recirculation system comprising expandable volumes, as described herein. As shown in FIG. 7, the pressure fluctuation dampening device may be used to generate periodic, pulsating flow with tunable frequency and amplitude.

As described herein, the devices and methods of the present invention may be used to control the pressure and/or flow rate of a fluid. In some embodiments, devices and/or systems of the invention may be selected to have a flow rate in the range from 1 nanoliter/second to 1 milliliter/second.

As used herein, a "processing device" may be any device capable of performing a chemical or biological process. For example, the processing device may perform chemical reaction, separation, extraction, filtration, incubation, crystallization, purification, or other chemical or biological process. In some cases, the chemical or biological processing device may be a reactor device, wherein the reactor device is capable of performing a chemical reaction, such as a catalytic reaction. The chemical reaction may be a homogeneous reaction or a heterogeneous reaction. In some cases, the processing device may comprise a heterogeneous catalyst, wherein recirculation of the interacting fluid over the heterogonous catalyst may enhance the performance of the processing device. In some embodiments, the processing device may perform a catalytic reaction, such as a homogeneous or heterogeneous catalytic reaction.

In some embodiments, the processing device may be a fluid separation device, able to perform fluid-fluid extraction or fluid-gas extraction. This technology may be useful in the design of compact systems (e.g., single chip systems) wherein small samples of biological fluids and/or materials may be analyzed. For example, the present invention may provide assays for toxin identification based on analysis of blood, saliva, tissues, and proteins, and/or DNA molecules extracted from these sources. In some cases, the fluid separation device may perform fluid gathering, filtering, mixing with reagents, and the like. In some cases, the processing device may enable mass transfer processes, and accurate analysis for other gas-liquid and liquid-liquid contacting applications, such as absorption, solvent removal, distillation, extraction and the like. In some cases, the processing device may remove condensation resulting from exhausts in a fuel cell. In some cases, the processing device may be used to analyze a sample, obtained by the evaporation of a volatile material. In some cases, the processing device may be used to reduce or substantially remove the occurrence of gas bubbles, such as air bubbles, in a microfluidic system. Other examples of fluid separation techniques are described in Günther, et al., *Langmuir* 2005, 21, 1547-1555, incorporated herein by reference.

Figure 8A:
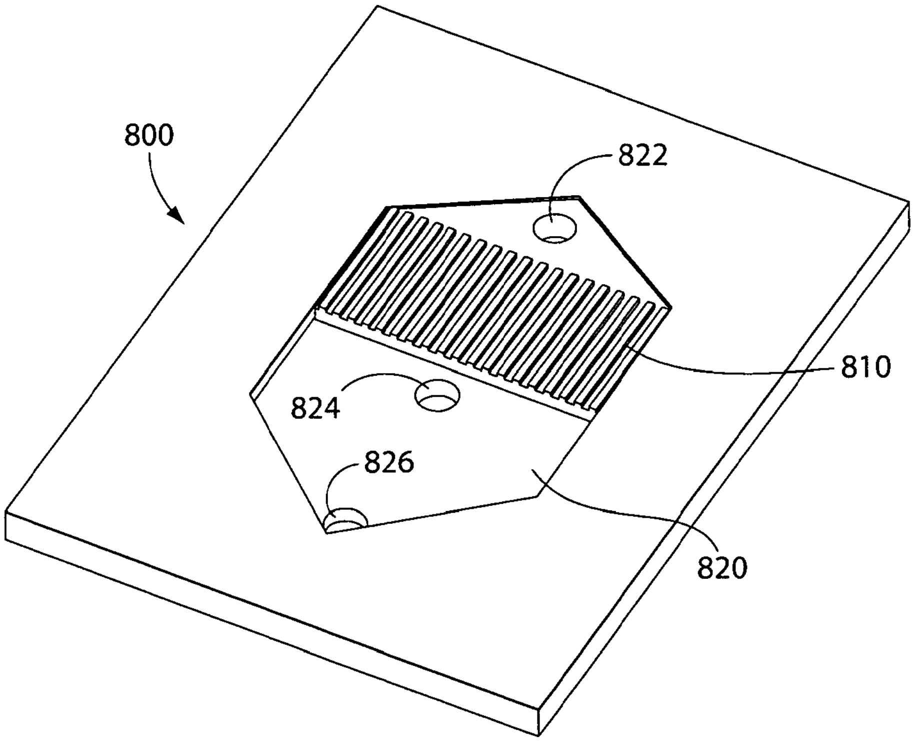
FIG. 8A shows an illustrative embodiment of an enclosure of the invention.
Figure 8B:
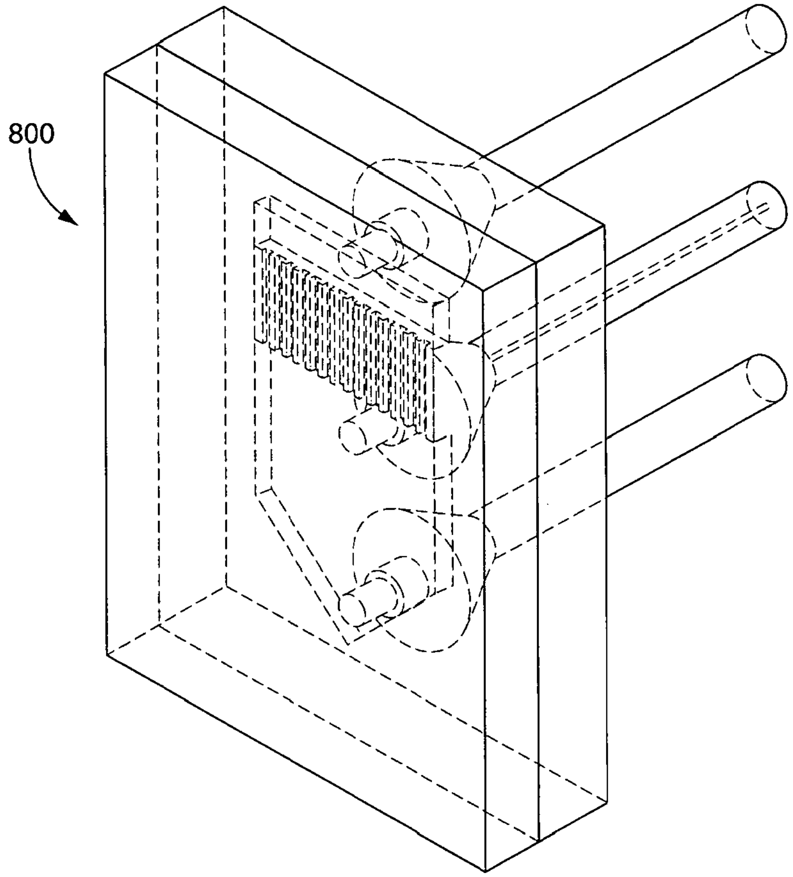
FIG. 8B shows a schematic representation of an enclosure fluidly incorporated into a device of the invention.

In some embodiments, devices and methods may comprise enclosures as described herein, wherein the enclosure may serve as a processing device. FIG. 8A shows an illustrative embodiment of an enclosure of the invention, wherein enclosure 800 contains an interior space 820, which can contain an interacting fluid, and a different interior space 810, shown in FIG. 8A to be positioned above space 820 and typically filled with a pressurizing fluid used to apply pressure to an interacting fluid in space 820 to effect flow. For example, an interacting fluid may be introduced to enclosure 800 via inlet 826, and a pressurizing fluid may be introduced via inlet 822 to urge movement of the interacting fluid out of space 820 via outlet 824. Space 810 may be constructed and arranged to be relatively shallow when compared to space 820, and/or may be positioned above the top surface of the interacting fluid in space 820, such that the interacting fluid remains in space 820 and/or flows out of space 820 via outlet 824 upon introduction of a pressurizing fluid, rather than flowing into space 810. In some cases, space 810 may comprise a plurality of narrow channels and/or capillaries positioned above the top surface of the interacting fluid in space 820, to allow flow of pressurizing fluid from inlet 822 to space 820, while preventing flow of interacting fluid into space 810. In some cases, enclosure 800 may be arranged such that an interacting fluid may be introduced to enclosure 800 via inlet 824, and a pressurizing fluid may be introduced via inlet 822 to urge movement of the interacting fluid out of space 820 via outlet 826. FIG. 8B shows a schematic representation of enclosure 800 fluidly connected to one or more conduits when incorporated into a device of the invention.

The enclosures may have any dimension suitable for use in a particular application. In some cases, the devices include at least one enclosure having a dimension of 0.01 cm, 0.05 cm, 0.1 cm, 0.5 cm, 1.0 cm, 3.0 cm, 5.0 cm, 10 cm, 50 cm, 100 cm, or greater. In an illustrative embodiment, the enclosure may have the dimensions, 2.0 cm×3.0 cm. It should be understood that, in other embodiments, the enclosure may have larger dimensions. The enclosures may be fabricated and/or enclosed or sealed using methods known in the art, including compression, sealing, braising, and the like. Also, the enclosures may be fabricated using any material suited for a particular application, including glass, polymer materials, particles (e.g., nanoparticles), metals, semiconductors, and the like. Those of ordinary skill in the art would be able to select the appropriate materials for use in a particular application.

Various components of the devices as described herein may comprise substantially rigid or essentially rigid materials, such as steel, glass, and/or SiN. The material may be selected to have a desired gas permeability, transparency, rigidity, and/or other desired property. For example, if the interacting fluid comprises biological molecules such as cells, some embodiments may comprise materials which are permeable by, for example, carbon dioxide or oxygen. In some cases, the substantially rigid material may have a gas permeability lower than the gas permeability of poly(dimethylsiloxane) (PDMS), under essentially identical conditions. The gas permeability of PDMS and/or materials used in the invention may be determined by methods known to those of ordinary skill in the art. For example, the oxygen permeability of PDMS may be determined by placing a film of PDMS in a sealed chamber such that the a first side of the PDMS layer contacts a first portion of the chamber and a second side of the PDMS layer contacts a second portion of the chamber. The chamber may be constructed and arranged to substantially prevent fluid flow between the first and the second portions of the chamber, except across the PDMS layer. A gas such as oxygen, for example, may be introduced into the first portion of the chamber, wherein the rate and/or concentration of oxygen which permeates the PDMS layer to reach the second chamber may be measured, thereby determining the gas permeability of PDMS.

Other components (e.g., conduits, enclosures, and the like) may be fabricated using methods known in the art, such as micromachining, lithography, and the like.

The devices and methods as described herein may further comprise other components, such as various sensors, controllers, optical fibers, membranes, valves, and the like, as required for a particular application.

As used herein, a "microfluidic device" is given its ordinary meaning in the art and refers to devices having components, such as conduits, channels, reservoirs, enclosures, and the like, which have maximum cross-sectional dimensions less than 2 mm, and in some cases, less than 1 mm. In one set of embodiments, components of embodiments of the invention are microfluidic or have a largest cross sectional dimension of no more than 2 mm or 1 mm. Of course, larger channels, tubes, chambers, reservoirs, etc. can be used to store fluids in bulk and to deliver fluids to components of the invention. In one set of embodiments, the maximum cross-sectional dimension of the components of embodiments of the invention are less than 500 microns, less than 200 microns, less than 100 microns, less than 50 microns, or less than 25 microns. In some cases the dimensions of the component may be chosen such that fluid is able to freely flow through the article or substrate. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As used herein, a "fluid" may refer to essentially any fluent material in a liquid, gas, and/or supercritical state. In some cases, the fluid is a pressurizing fluid (e.g., a gas), as described herein. In some cases, the fluid is an interacting fluid. As used herein, the term "interacting fluid" refers to a fluid comprising at least one component able to undergo a chemical or biological process (e.g., chemical reaction, separation, etc.). The interacting fluid and chemical or biological processing device may be selected in combination with each other to carry out a particular chemical or biological process. For example, the interacting fluid may comprise components able to be separated from one another upon contact with a particular surface in a separation device. In one embodiment, the interacting fluid may comprise a biological molecule such as a cell, wherein the cell may contact a surface in the separation device and adhere to the surface, such that the cell may be separated from the remainder of the interacting fluid. In another example, the interacting fluid may comprise a chemical compound or other chemical substrate able to react with a catalyst contained within a reactor device, or other reagent introduced into the reactor device for the purpose of reacting with the chemical compound or chemical substrate. That is, an interacting fluid does not refer to a fluid which, over time, may inherently react with, for example, steel, glass, SiN, material used for an expandable volume, or other component of the device which the fluid may contact.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to, the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A fluid pressure regulator able to affect pressure of a chemically or biologically interacting fluid passing from a first chemical or biological processing device to a second chemical or biological processing device, comprising:

a pressure regulator inlet fluidly connected to the first chemical or biological processing device;

a pressure regulator outlet fluidly connected to the second chemical or biological processing device;

at least two enclosures, each enclosure constructed to contain the chemically or biologically interacting fluid, and each enclosure positioned between and fluidly connected to both the first chemical or biological processing device and the second chemical or biological processing device via the pressure regulator inlet and the pressure regulator outlet, respectively;

a source of a pressurizing fluid in communication with the at least two enclosures, whereby the pressurizing fluid applies pressure to the interacting fluid to urge movement of the interacting fluid relative to each respective enclosure through the outlet to the second processing device; and at least one one-way valve in a conduit between the pressure regulating inlet and the pressure regulating outlet, positioned to allow fluid flow preferentially in a direction from the inlet toward the outlet, wherein, in operation, the interacting fluid has a first pressure and/or flow rate in the pressure regulator inlet and a second pressure and/or flow rate in the pressure regulator outlet, wherein the second pressure and/or flow rate can be made by the device to be greater than the first pressure and/or flow rate.

2. A fluid pressure regulator as in claim 1, comprising at least one one-way valve in a conduit between the pressure regulating inlet and an enclosure, positioned to allow fluid flow preferentially in a direction from the pressure regulating inlet toward the enclosure, and at least one one-way valve in a conduit between the pressure regulating outlet and an enclosure, positioned to allow fluid flow preferentially in a direction from the enclosure toward the pressure regulating outlet.

3. A fluid pressure regulator as in claim 1, wherein the valve is a continuous valve.

4. A fluid pressure regulator as in claim 1, wherein the valve is a non-continuous valve.

5. A fluid pressure regulator as in claim 1, wherein the pressurizing inlet comprises one or more than one conduit fluidly connected to at least one enclosure.

6. A fluid pressure regulator as in claim 1, wherein the pressurizing outlet comprises one or more than one conduit fluidly connected to at least one enclosure.

7. A fluid pressure regulator as in claim 1, wherein the chemical or biological processing device is a reactor device.

8. A fluid pressure regulator as in claim 7, wherein the reactor device is capable of performing a catalytic reaction.

9. A fluid pressure regulator as in claim 1, wherein the chemical or biological processing device is a separation device.

10. A fluid pressure regulator as in claim 9, wherein the separation device is capable of performing a fluid-fluid separation or a fluid-gas separation.

11. A fluid pressure regulator as in claim 1, wherein at least enclosure is a reactor device.

12. A fluid pressure regulator as in claim 1, comprising a first enclosure and a second enclosure, each enclosure constructed to contain the chemically or biologically interacting fluid, and each fluidly connected to both the pressure regulator inlet and the pressure regulator outlet wherein the first enclosure and the second enclosure are switchable between an on and an off state with respect to the pressurizing fluid.

13. A fluid pressure regulator as in claim 1, wherein the pressurizing fluid is a gas.

14. A fluid pressure regulator as in claim 1, wherein the pressurizing fluid is oxygen, nitrogen, or argon.

15. A fluid pressure regulator as in claim 1, wherein the fluid pressure regulator comprises a substantially rigid material.

16. A fluid pressure regulator as in claim 15, wherein the substantially rigid material is steel, glass, or silicon nitride.

17. A fluid pressure regulator as in claim 15, wherein the substantially rigid material has a gas permeability lower than the gas permeability of poly(dimethylsiloxane), under essentially identical conditions.

18. A fluid pressure regulator as in claim 1, further comprising at least one pressure release valve to release pressurizing fluid in association with at least one enclosure and/or the source of pressurizing fluid.

19. A fluid pressure regulator as in claim 1, wherein the fluid pressure regulator is arranged in a microfluidic device.

* * * * *